(12) United States Patent
Spaner

(10) Patent No.: US 6,733,748 B2
(45) Date of Patent: May 11, 2004

(54) CHRONIC LYMPHOCYTIC LEUKEMIA TREATMENT

(75) Inventor: David Elliott Spaner, Toronto (CA)

(73) Assignee: Vasogen Ireland Limited, Shannon (IE)

(*) Notice: Subject to any disclaimer, the term of this patent is extended or adjusted under 35 U.S.C. 154(b) by 0 days.

(21) Appl. No.: 09/999,850

(22) Filed: Oct. 25, 2001

(65) Prior Publication Data

US 2002/0090358 A1 Jul. 11, 2002

(30) Foreign Application Priority Data

Oct. 25, 2000 (CA) .............................................. 2324199

(51) Int. Cl.⁷ .......................... A01N 65/00; A23K 1/17; A61K 1/18
(52) U.S. Cl. ........................ 424/93.7; 424/442; 424/439
(58) Field of Search ................................ 424/93.7, 442, 424/439

(56) References Cited

FOREIGN PATENT DOCUMENTS

| WO | 96/40214 | 12/1996 |
|----|----------|---------|
| WO | 98/07436 | 2/1998 |
| WO | 99/24078 | 5/1999 |
| WO | 00/06703 | 2/2000 |
| WO | WO 00/06703 * | 2/2000 |
| WO | 00/41705 | 7/2000 |
| WO | 01/55348 | 8/2001 |

* cited by examiner

Primary Examiner—Brenda Brumback
Assistant Examiner—Randall Winston
(74) Attorney, Agent, or Firm—Swiss Law Group

(57) ABSTRACT

Chronic lymphocytic leukemia (CLL) in a patient is treated by administering to the patient oxidatively stressed CLL cells. The CLL cells are oxidatively stressed extracorporeally, e.g. by subjection to oxygen/ozone mixtures, and preferably are simultaneously subjected to other stressors such as UV light. Preferably also, the CLL cells are autologous, and are contained in an aliquot of the patient's blood at the time of subjection to stressing.

19 Claims, No Drawings

CHRONIC LYMPHOCYTIC LEUKEMIA TREATMENT

CROSS REFERENCE TO RELATED APPLICATIONS

This application claims the benefit of Canadian Application Serial Number 2,324,199, filed Oct. 25, 2000, which is incorporated by reference in its entirety.

FIELD OF THE INVENTION

This invention relates to leukemia alleviation, and to processes and cellular compositions useful therein. More specifically, it relates to compositions and processes for alleviating chronic lymphocytic leukemia in mammalian patients, especially humans, and to processes for preparing such compositions.

BACKGROUND OF THE INVENTION

Chronic lymphocytic leukemia (hereinafter CLL) is one of the four major types of leukemia encountered by humans, the others being acute lymphocytic leukemia, acute myeloid leukemia and chronic myeloid leukemia. CLL is most commonly encountered in patients over the age of sixty. It has a gradual onset, and may not cause the patient discomfort or pain for several years. It is characterized by a large number of cancerous mature lymphocytes and enlarged lymph nodes. Cancerous cells crowd out the normal cells in the bone marrow and lymph nodes. Anemia develops in the patient and the number of normal white cells and platelets in the patient's blood decreases, whereas the total white cell count increases due to the proliferation of abnormal white cells. The level and activity of antibodies also decrease. As a result, the patient's immune system becomes compromised. It is more common for CLL sufferers to die from consequences of the compromised immune system, e.g. infections, than from the CLL itself.

The most common type of CLL is a B cell leukemia, and the malignant cell of origin is a CD5+B cell, i.e. a B cell expressing the marker CD5.

Clinical stage of CLL, characterized in the staging systems of Rai (stages O-IV) and Binet (stages A-C), remains the strongest predictor of survival in CLL patients. Both systems are based on the amount of involved lymphoid tissue and the presence of anemia and/or thrombocytopenia. In general, patients with later stages have a significantly worse prognosis and a shorter survival. Patients with Rai stage IV or Binet stage C have a median survival of only 1.5 to 2 years.

Chemotherapy (initially with alkylating agents such as chlorambucil and subsequently with fludarabine) is the standard treatment for CLL. A patient diagnosed with CLL is normally monitored by tracking the white cell count in the blood. Chemotherapy is not instituted until the patient starts to suffer symptoms such as fatigue, weight loss, fevers or pain as a result of the progression of the CLL. However, CLL is not curable with conventional methods of chemotherapy, even though initial response rates are high. The toxicities associated with the use of chemotherapy are well known and include nausea and myelosuppression with a risk of developing serious infections. Moreover, subsequent responses become inexorably short-lived, likely because drug-resistant tumor cells are selected by the use of cytotoxic agents.

Accordingly, it is an object of the present invention to provide novel procedures and compositions for alleviation of CLL in mammalian patients.

It is a further object of the invention to provide procedures and compositions which, on suitable administration to a CLL suffering patient, will significantly postpone the need for subjecting the patient to chemotherapy.

SUMMARY OF THE INVENTION

According to the present invention in its broad aspects, CLL in a mammalian patient is alleviated by administering to the patient oxidatively stressed CLL malignant cells. The source of the CLL malignant cells may be the mammalian patient himself or herself (e.g. a withdrawn blood sample from the patient), a compatible mammalian donor (e.g. a withdrawn blood sample from another, compatible CLL-suffering patient), or a cultured cell line of CLL malignant cells. Subjection of the CLL malignant cells to oxidative stress takes place in vitro. The oxidatively stressed CLL cells thus obtained are administered to the patient to result in an alleviation of the patient's CLL.

According to a preferred aspect of the present invention, CLL in a mammalian patient suffering therefrom is significantly alleviated by administering to the patient oxidatively stressed blood cells, including oxidatively stressed CLL malignant cells, obtained from the patient and subjected to oxidative stress in vitro and then reintroduced into the patient. The procedure thus involves extracting an appropriate quantity of blood containing CLL cells from the CLL patient, treating the blood or a selected portion of it extracorporeally with an oxidative stressor, and reintroducing it into the same patient. The result, after one or more of such treatments, is a significant alleviation of the patient's CLL condition, as indicated in a reduced white blood cell proliferation and a reduced swelling of lymph nodes of the patient.

Thus from one aspect, the present invention provides a process for treating a CLL suffering patient for alleviation of CLL, which comprises extracting an aliquot of blood containing CLL cells from the patient, subjecting at least a portion of the extracted blood cells extracorporeally to appropriate oxidative stress, and re-introducing the oxidatively-stressed material into the patient.

Another aspect of the present invention is oxidatively stressed mammalian CLL cells, useful for introduction into a mammalian patient suffering from CLL to alleviate the patient's CLL.

A further aspect of the present invention is the use in preparation of a medicament active against CLL in a mammalian patient, of oxidatively stressed autologous blood or blood fractions, including oxidatively stressed autologous malignant CLL cells.

Another aspect of this invention is a composition comprising stressed CLL cells. The cells may be oxidatively stressed and may further be autologous CLL cells.

While it is not intended that this invention should be limited to any particular mode of action or theory of mechanism or performance, it is postulated that appropriately oxidatively stressed blood cells activate the regulatory immune T cells controlling the CD5+B cells in the patient's blood, including the malignant CD5+B cells. The oxidatively stressed cells, on reintroduction into the CLL patient, are believed to activate certain T cells present in the patient's blood which then down-regulate the malignant CD5+B cells by acting directly on them or by secreting cytokines which then act on them. In any event, the result is a significant reduction in the rate of proliferation of the malignant CD5+B cells in the CLL patient and a consequent alleviation of the CLL condition and its symptoms.

DESCRIPTION OF THE PREFERRED EMBODIMENTS

A preferred embodiment of the present invention subjects the blood cells, or the appropriate fraction of them including the CLL cells, to electromagnetic emission radiation as well as oxidative stress, either simultaneously or sequentially. Optionally also, a temperature stressor may be applied to the cells, simultaneously or sequentially with the oxidative stressor and the electromagnetic emission stressor, i.e. a temperature at, above or below body temperature. An aliquot of blood is drawn from the CLL patient, of volume up to about 400 ml, preferably from about 0.1 to 100 ml, more preferably from about 1 to about 15 ml, even more preferably from about 8 to about 12 ml. Either the whole blood is subjected to the stressor(s), or an appropriate cellular fraction thereof containing the CLL malignant B cell fraction is separated by known methods and subjected to the aforementioned stressor(s). The stressed cells are then reintroduced into the CLL patient from whom the original aliquot was drawn. The term "aliquot" as used herein refers to the sample subjected to the stressors; and embraces both the originally extracted whole blood and any fraction thereof subjected to stressors, before or after separation.

The modified aliquot is re-introduced into the patient's body by any suitable method, most preferably intramuscular injection, but also including subcutaneous injection, intraperitoneal injection, intra-arterial injection, intravenous injection and oral administration. Accordingly, the composition may optionally include a pharmaceutically acceptable excipient, such as sterile physiological saline.

Preferably also, the aliquot of blood is in addition subjected to mechanical stress. Such mechanical stress is suitably that applied to the aliquot of blood by extraction of the blood aliquot through a conventional blood extraction needle, or a substantially equivalent mechanical stress, applied shortly before the other chosen stressors are applied to the blood aliquot. This mechanical stress may be supplemented by the mechanical stress exerted on the blood aliquot by bubbling gases through it, such as ozone/oxygen mixtures, as described below.

The optionally applied temperature stressor either warms the aliquot being treated to a, temperature above normal body temperature or cools the aliquot below normal body temperature. The temperature is selected so that the temperature stressor does not cause excessive hemolysis in the blood contained in the aliquot and so that, when the treated aliquot is injected into a subject, the desired effect will be achieved. Preferably, the temperature stressor is applied so that the temperature of all or a part of the aliquot is up to about 55° C., and more preferably in the range of from about −5° C. to about 55° C.

In some preferred embodiments of the invention, the temperature of the aliquot is raised above normal body temperature, such that the mean temperature of the aliquot does not exceed a temperature of about 55° C., more preferably from about 40° C. to about 50° C., even more preferably from about 40° C. to about 44° C., and most preferably about 42.5±1° C.

In other preferred embodiments, the aliquot is cooled below normal body temperature such that the mean temperature of the aliquot is within the range of from about 4° C. to about 36.5° C., more preferably from about 10° C. to about 30° C., and even more preferably from about 15° C. to about 25° C.

The oxidative environment stressor can be the application to the aliquot of solid, liquid or gaseous oxidizing agents, including peroxides such as hydrogen peroxide. Preferably, it involves exposing the aliquot to a mixture of medical grade oxygen and ozone gas, most preferably by applying to the aliquot medical grade oxygen gas having ozone as a component therein. The ozone content of the gas stream and the flow rate of the gas stream are preferably selected such that the amount of ozone introduced to the blood aliquot, either on its own or in combination with one of the other stressors, does not give rise to excessive levels of cell damage, and so that, when the treated aliquot is injected into a subject, the desired effect will be achieved. Suitably, the gas stream has an ozone content of up to about 300 $\mu$g/ml, preferably up to about 100 $\mu$g/ml, more preferably about 30 $\mu$g/ml, even more preferably up to about 20 $\mu$g/ml, particularly preferably from about 10 $\mu$g/ml to about 20 $\mu$g/ml, and most preferably about 14.5±1.0 $\mu$g/ml. The gas stream is suitably supplied to the aliquot at a rate of up to about 2.0 liters/min, preferably up to about 0.5 liters/min, more preferably up to about 0.4 liters/min, even more preferably up to about 0.33 liters/min, and most preferably about 0.2±0.025 liters/min. The lower limit of the flow rate of the gas stream is preferably not lower than 0.01 liters/min, more preferably not lower than 0.1 liters/min. Preferably the amount of ozone introduced to the blood does not exceed about 300 $\mu$g/ml of blood in the aliquot.

The electromagnetic emission stressor is suitably applied by irradiating the aliquot under treatment from a source of electromagnetic emission while the aliquot is maintained at the aforementioned temperature and while the oxygen/ozone gaseous mixture is being bubbled through the aliquot. Preferred electromagnetic emissions are selected from photonic radiation, more preferably UV, visible and infrared light, and even more preferably UV light. The most preferred UV sources are UV lamps emitting UV-C band wavelengths, i.e. at wavelengths shorter than about 280 nm. Ultraviolet light corresponding to standard UV-A (wavelengths from about 315 to about 400 nm) and UV-B (wavelengths from about 280 to about 315) sources can also be used. As in the case of the oxidative stressor, the UV dose should be selected, on its own or in combination of the other chosen stressor(s), so that excessive amounts of cell damage do not occur, and so that, when the treated aliquot is injected into a subject, the desired effect will be achieved. For example, an appropriate dosage of such UV light, can be obtained from lamps with a power output of from about 15 to about 25 watts arranged to surround the sample container holding the aliquot, each lamp providing an intensity, at a distance of 1 meter, of from about 45 to 65 mW/cm$^2$. Up to eight such lamps, surrounding the sample container holding the aliquot, with a combined output at 253,7 nm of 15 to 25 watts, operated at an intensity to deliver a total UV light energy at 253.7 nm at the surface of the blood of from about 0.025 to about 10 joules/cm$^2$, preferably from about 0.1 to about 3.0 joules/cm$^2$ may advantageously be used. Such a treatment, applied in combination with the oxidative environment stressor, provides a modified blood aliquot which is ready for injection into the subject.

It is preferred to subject the aliquot to the oxidative environment stressor, the UV light stressor and the temperature stressor simultaneously, following the subjection of the aliquot to the mechanical stress, e.g. by extraction of the blood from the patient. Thus, the aliquot may be maintained at a predetermined temperature above or below body temperature while the oxygen/ozone gas mixture is applied thereto and while it is irradiated with ultraviolet light.

The time for which the aliquot is subjected to the stressors is normally within the time range of from about 0.5 minutes up to about 60 minutes. The time depends to some extent upon the chosen combination of stressors. When UV light is used, the intensity of the UV light may affect the preferred time. The chosen temperature level may also affect the preferred time. When the oxidative environment in the form of a gaseous mixture of oxygen and ozone applied to the aliquot is chosen as one of the two stressors, the concentration of the oxidizing agent and the rate at which it is supplied to the aliquot may affect the preferred temperature. Some experimentation to establish optimum times may be necessary on the part of the operator, once the other stressor levels have been set. Under most stressor conditions, preferred times will be in the approximate range of from about 2 to about 5 minutes, more preferably about 3 minutes. The starting aliquot temperature, and the rate at which it can be warmed or cooled to a predetermined temperature, tends-to vary from subject to subject. Warming is suitably by use of one or more infrared lamps placed adjacent to the aliquot container. Other methods of warming can also be adopted.

As noted, it is preferred to subject the aliquot of blood to a mechanical stressor, as well as the chosen stressor(s) discussed above. Extraction of the blood aliquot from the patient through a hypodermic needle constitutes the most convenient way of obtaining the aliquot for further extracorporeal treatment, and this extraction procedure imparts a suitable mechanical stress to the blood aliquot. The mechanical stressor may be supplemented by subsequent processing, for example the additional mechanical shear stress caused by bubbling as the oxidative stressor is applied.

In the practice of the preferred process of the present invention, the aliquot may be treated with the heat, UV light and oxidative environment stressors using an apparatus of the type described in U.S. Pat. No. 4,968,483 to Mueller. The aliquot is placed in a suitable, sterile container, which is fitted into the machine. A UV-permeable container is used and the UV lamps are switched on for a fixed period before the other stressor is applied, to allow the output of the UV lamps to stabilize. When a temperature stressor is used in the combination, the UV lamps are typically on while the temperature of the aliquot is adjusted to the predetermined value, e.g. 42.5±1° C. Four UV lamps are suitably used, placed around the container.

In the preferred method of the invention, a mammalian patient is given one or more courses of treatments, each course of treatment comprising the administration to a mammalian subject of one or more (e.g. one to six) blood originating aliquots modified as disclosed above. The treatment may be administered daily, but no more than one treatment should be administered to the subject per clay.

Although it may be sufficient to administer only one course of treatment as described above to the subject, it may be preferred in some circumstances to administer more than one treatment or course of treatment, or to follow the above-described course of treatment by periodic "booster" treatments, if necessary, to maintain the desired effects of the present invention. There may be a substantial interval between individual treatments or courses of treatment. For example, it may be preferred to administer booster treatments at intervals of 1 week, 1 month, 3 months or 6 months or other appropriate periods following the initial treatment or course of treatment, depending upon the condition of the individual patient and the progression or remission of the CLL. Regular periodic monitoring of the patients undergoing the treatment according to the invention is contemplated, with repeats of the treatment or course of treatment as indicated by the patient's condition and as determined by the attending physician.

The process of the present invention is particularly indicated for CLL patients whose condition shows signs of accelerated progression to the point where chemotherapy would normally be instituted. Patients may be selected for treatment based upon several criteria. For example, patients having a CLL cell count in the blood of from about 20 million—100 million CLL cells per milliliter of blood are preferred candidates for the treatment. Normally, however, progression of CLL after diagnosis is simply monitored by determining the white blood cell count of a patient. A normal healthy patient has a white blood cell count of about 10 (i.e. $10 \times 10^6$ white cells per ml of blood), whereas a CLL patient has elevated white blood cell counts. As the CLL condition progresses, the patient's white blood cell count increases, mainly due to the proliferation of the malignant CD5+B cells. When the patient's white blood cell count reaches the approximate range $30 \times 10^6$ to $100 \times 10^6$, institution of chemotherapy may be indicated. This is the indicator for the institution of the process of the present invention, in its preferred applications, as a means of forestalling or at least delaying the application of chemotherapy to the patient, with all its undesirable accompanying effects.

Patients may be selected for treatment with the methods and processes of this invention. An assessment by an attending clinician will determine their suitability, but normally it will be a patient who has previously tested positive for CLL, has been monitored for some time without evidencing an increase in white cell count, but who has, in the previous 1–2 months prior to test evidenced a white blood cell count increase into the $30 \times 10^6$ to $100 \times 10^6$ approximate range.

The beneficial effects of the process of the present invention, as with most leukemia treatments, vary widely in efficacy between individual patients. Some patients show an immediate and long lasting effect. Others show an immediate effect which wears off over time, but which can be re-effected by undertaking a further course of treatments according to the invention. In others, the immediate effect wears off, and apparently is not so re-effected. In any event, the need for the patient to undergo chemotherapy treatments is either obviated or delayed in substantially all cases. Treatment according to the invention can also beneficially follow or even accompany chemotherapy.

The invention will be further described, for illustrative purposes, with reference to specific examples of clinical application of the processes and products of specifically preferred embodiments of the invention.

EXAMPLE 1

An elderly male patient had been diagnosed with CLL three years earlier, and had been continuously monitored by physicians since that time, with a view to instituting chemotherapy treatments when the condition deteriorated to the appropriate extent. In the eight-month period leading up to the treatments in accordance with the invention, the patient's white blood cell count had increased from 30 to 70, indicating an imminent need to institute chemotherapy. The patient also exhibited significantly swollen lymph nodes.

The patient was given a course of treatments in accordance with the invention. Each treatment involved withdrawing a 10 ml aliquot of blood from the patient via venal puncture, subjecting the whole blood aliquot, in a sterile UV-transparent container and in the presence of anticoagulant, to simultaneous ozone-oxygen bubbling and UV radiation exposure at elevated temperature, in an apparatus essentially as described in aforementioned U.S. Pat. No. 4,968,483. The treated blood was re-administered to the patient by injection into the gluteal muscle.

The temperature of the blood aliquot in the apparatus was initially raised to 42.5° C. and held steady at that level. The constitution of the gas mixture was 14–15 mcg/ml ozone/oxygen, fed through the aliquot at a rate of about 200 mls/minute, for three minutes. The UV radiation had a wavelength of 253.7 nm.

After a course of 6 such treatments, administered over three weeks with a two or three-day interval between each treatment, a favorable response was noted. Instead of a continuing increase in white cell count, the patient exhibited a decrease, from 70 to 61. There was also a 50% decrease in peripheral adenopathy. The treatments were well tolerated and no significant side effects have been reported by the patient.

EXAMPLE 2

Following the protocol described in Example 1, the following patients have been treated.

A 55-year old man suffering from CLL and diabetes was treated. The increase in his white cell count was arrested, an effect which has lasted one month since the end of treatment.

A 50-year old man suffering from CLL was treated. His white blood cell count dropped from 30 to 15. This lower level has been maintained for at least one month after the conclusion of treatment.

A 50-year old woman suffering from CLL was treated. She had been treated previously for CLL by chemotherapy using Chlorambucil. Her condition had relapsed and the Chlorambusil was no longer effective. After treatment with the above protocol her white blood cell count was stabilized.

A 60-year old man with CLL and heart problems was treated. His white cell count of 30 was stabilized by the course of treatment.

What is claimed is:

1. A method for treating Chronic Lymphocytic Leukemia (CLL) in a patient in need thereof, which comprises removing an aliquot of blood containing CLL cells from the patient, subjecting at least a portion of the removed blood aliquot extracorporeally to appropriate oxidative stress, wherein the oxidative stress comprises application of an effective concentration of an oxidizing agent to the CLL cells and re-introducing at least a portion of the oxidatively stressed aliquot into the patient.

2. A method of claim 1, wherein the oxidatively stressed aliquot includes malignant CLL cells.

3. The method of claim 2, wherein the cells are further subjected to UV radiation.

4. The method of claim 1, wherein the aliquot of blood has a CLL cell content of from about 20 million to about 100 million cells per ml of blood.

5. The method of claim 1, wherein the aliquot of blood has a white blood cell count of from about $30 \times 10^6$ to about $100 \times 10^6$.

6. The method of claim 1, wherein oxidizing agent comprises ozone gas, and the ozone gas is introduced to the CLL cells in an amount which does not give rise to excessive levels of cell damage.

7. The method of claim 1, wherein the oxidizing agent comprises a mixture of ozone gas and medical grade oxygen, the ozone gas being contained in the mixture in a concentration of up to about 300 μg/ml.

8. The method of claim 6, wherein the ozone gas is contained in the mixture in a concentration of up to about 30 μg/ml.

9. The method of claim 6, wherein the ozone gas is contained in the mixture in a concentration of from about 13.5 μg/ml to about 15.5 μg/ml.

10. The method of claim 7, wherein the mixture is applied to the CLL cells at a flow rate of up to 0.33 liters/mm.

11. The method of claim 7, wherein the mixture is applied to the CLL cells at a flow rate of from about 0.21 liters/min to about 0.27 liters/min.

12. The method of claim 3, wherein the UV radiation comprises UV light having one or more UV-C band wavelengths.

13. The method of claim 1, further comprising applying temperature stressor to the CLL veils such that the temperature to which the CLL cells are cooled or heated is a temperature which does not result in substantial lysis of the CLL cells.

14. The method of claim 13, wherein the temperature stressor is applied so that the temperature of at least part of the CLL cells is in the range of from about −5° C. to about 55° C.

15. The method of claim 13, wherein the mean temperature of the CLL cells is in the range of from about 37° C. to about 44° C.

16. The method of claim 14, wherein the temperature of the CLL cells is in the range of from about 37° C. to about 55° C.

17. The method of claim 16, wherein the temperature of the CLL cells is 42.5±1° C.

18. The method of claim 1, wherein the CLL cells are subjected to oxidative stress for a period of up to about 60 minutes.

19. The method of claim 18, wherein the CLL cells are subjected to oxidative stress for a period of about 3 minutes.

* * * * *